United States Patent [19]

Nakano et al.

[11] Patent Number: 6,127,579
[45] Date of Patent: Oct. 3, 2000

[54] METHOD OF MANUFACTURING 1-INDANONE

[75] Inventors: Shigeru Nakano; Noriko Yoneta; Takashi Tate, all of Fukushima-ken, Japan

[73] Assignee: Ichikawa Gosei Chemical Co., Ltd., Tokyo, Japan

[21] Appl. No.: 09/345,980

[22] Filed: Jul. 1, 1999

[30] Foreign Application Priority Data

Jul. 3, 1998 [JP] Japan .................................. 10-188785

[51] Int. Cl.⁷ ............................ C07C 45/30; C07C 43/02
[52] U.S. Cl. .......................... 568/323; 568/322; 568/330; 568/661
[58] Field of Search ..................................... 568/322, 323, 568/330, 327, 661; 549/356, 381

[56] References Cited

U.S. PATENT DOCUMENTS 5,841,000  11/1998  Igarashi et al. ......................... 568/808

FOREIGN PATENT DOCUMENTS 9-301940  11/1997  Japan .
10-072398   3/1998  Japan .

OTHER PUBLICATIONS

"Efficient Intramolecular General Acid Catalysis of Enol Ether Hydrolysis, Hydrogen–bonding Stabilisation of the Transition State for Proton Transfer to Carbon", J. Chem. Soc., Perkin Trans 2, 1994, by Anthony J. Kirby et al.
"Chromium(II)—catalyzed Electrochemical Dehalogenation of β–Hydroxyhalides—Convenient Entry to Deoxynucleosides", Agnew. Chem. Int. Ed. 1980; vol. 19(1), pp. 46–47, by Wellman et al.
"Tautomerism of the Monohydroxy Derivatives of Five–Membered O, N, S Heterocycles", J. Am. Chem. Soc. 1989; vol. 111, pp. 5346–5356, by Brian Capon et al.

"Some Bromine Derivatives of Indene and Indane", Journal of the American Society, vol. 57, 1935, pp. 2022–2026, by H.D. Porter et al.

Primary Examiner—Sreeni Padmanabhan
Attorney, Agent, or Firm—Frommer Lawrence & Haug LLP

[57] ABSTRACT

A method of manufacturing the useful substance 1-indanone from easily obtainable materials consists of reacting an indanyl ether represented by the generic formula

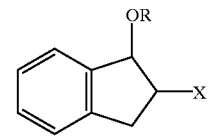

(I)

under basic conditions to give a novel substance which is the indenyl ether derivative represented by the generic formula

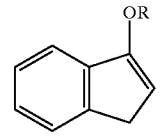

(II)

and hydrolyzing this to give the 1-indanone represented by the generic formula

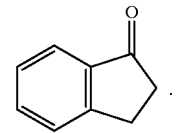

(III)

12 Claims, No Drawings

METHOD OF MANUFACTURING 1-INDANONE

BACKGROUND OF THE INVENTION

1. Field of the Invention

This invention relates to an industrially useful method of manufacturing 1-indanone.

2. Description of the Related Art

The compound 1-indanone is an important drug intermediate. For example, J. Org. Chem. 55, 4237 (1990) discloses that this compound is a useful intermediate in the manufacture of serotonin reuptake inhibitors. Several conventional methods of manufacturing 1-indanone have been disclosed. For example, the inventors have invented a method of obtaining 1-indanone by manufacturing N-indenyl amides from N-indanyl amides and then hydrolyzing them (Japanese Unexamined Patent Publication No. 10(1998)-72398). This method is simple and the desired 1-indanone is obtained with a good yield. However, the raw material of N-indanyl amides are manufactured as byproducts of the Ritter reaction in the method of manufacturing cis-1-amino-2-benzo cycloalkanols for which the inventors have a previous patent applied for (Japanese Unexamined Patent Publication No. 9(1997)-301940), and thus the yield is low. Also, since there is no other known method of manufacturing n-indanyl amides, difficulties are predicted in maintaining a stable supply of N-indanyl amides as the raw material for 1-indanone.

SUMMARY OF THE INVENTION

The object of the invention is to provide an effective method of manufacturing 1-indanone.

The inventors previously invented a method of obtaining 1-indanone by hydrolyzing N-indenyl amides (Japanese Unexamined Patent Publication No. 10(1998)-72398). Here follows an explanation of the reaction mechanism when 1-acetamidoindene (VII) is used as an example of the N-indenyl amide. As shown below, they thought that protonation of 1-acetamidoindene (VII) produces an indanyl cation at position 1 on an indane ring, and after water is added, the acetamide group is eliminated, thus forming 1-indanone. To wit, they pursued studies with the idea of synthesizing by some method a 1-substituent indene with a removable substituent at position 1 on an indane ring and hydrolyzing this to obtain 1-indanone.

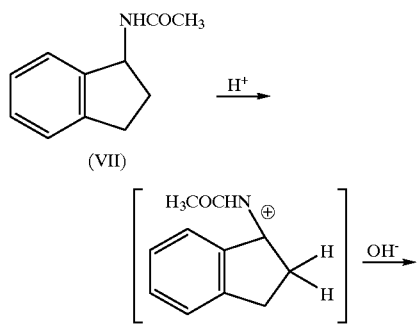

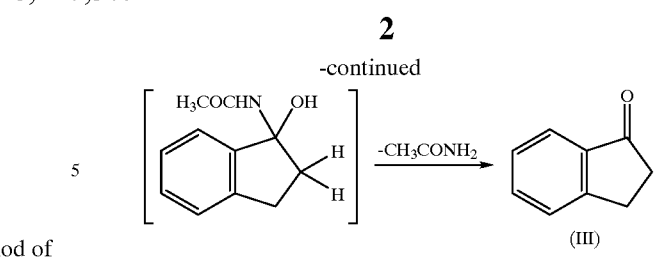

As a result, the inventors considered that since 2-haloindan-1-ols undergo a hydrogen halide elimination reaction under basic conditions, a 2-haloindan-1-ol ring would be a suitable substrate. Moreover, if trans-2-bromoindan-1-ol (manufactured by the inventor's method according to Japanese Unexamined Patent Publication No. 8(1996)-245455) undergoes an HBr elimination reaction to form 1,2-epoxyindane, they thought this product also can be used as an 1-alkyloxyindan-2-ol by employing an alkali metal alkoxide following known methods and changing it to an appropriate substrate by replacing the hydroxyl group in position 2 with a removable substituent.

The inventors used these indanyl ethers given in generic formula (I), and studied in detail the conditions under which unsaturated bonds form by 1,2-elimination and thus perfected the invention. To wit, the invention provides a method of manufacturing 1-indanone comprising the steps of reacting an indanyl ether represented by generic formula (I)

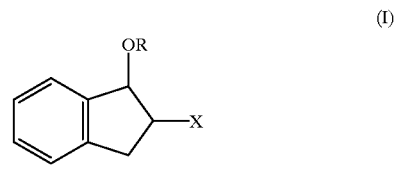

(where, in the formula, R is a straight-chain or branched-chain lower alkyl group with a carbon number of 1–5 or an alkoxyalkyl group represented by $CH(OR_2)R_1$; $R_1$ and $R_2$ are straight-chain or branched-chain lower alkyl groups with a carbon number of 1–5; $R_1$ and $R_2$ may be identical or different; $R_1$ and $R_2$ may also be connected to form a ring; X is a halogen atom or substituent sulfonyloxy group represented by $OSO_2R_3$; $R_3$ is a substituent or non-substituent phenyl group or a lower alkyl group with a carbon number of 1–5; OR and X may have the cis-arrangement or the trans- arrangement; and it may be in racemic form or optically active form) under basic conditions to give an indenyl ether derivative represented by generic formula (II)

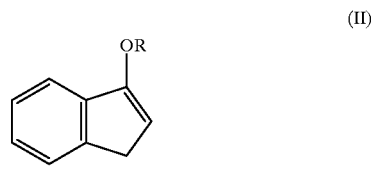

(where, in the formula, R is defined identically to that in generic formula (I) above) and hydrolyzing this to give the 1-indanone represented by generic formula (III)

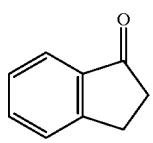

(III)

The indenyl ether derivative represented by generic formula (II) and manufactured according to the invention is a novel compound. To wit, the inventors discovered a method of manufacturing a novel indenyl ether derivative represented by generic formula (II) and that this compound can be hydrolyzed so that the useful compound 1-indanone represented by formula (III) can be easily synthesized, and thus perfected the invention.

Here follows a further explanation of the invention in detail.

Examples of the indanyl ethers represented by generic formula (I) include: 2-chloro-1-(1-methoxyethoxy)indane, 2-chloro-1-(1-ethoxyethoxy)indane, 2-chloro-1-(1-propoxyethoxy)indane, 2-chloro-1-(1-isopropoxyethoxy)indane, 2-chloro-1-(1-butoxyethoxy)indane, 2-chloro-1-(1-isobutoxyethoxy)indane, 2-chloro-1-(1-pentoxyethoxy)indane, 2-chloro-1-(1-isopentoxyethoxy)indane, 2-bromo-1-(1-methoxyethoxy)indane, 2-bromo-1-(1-ethoxyethoxy)indane, 2-bromo-1-(1-propoxyethoxy)indane, 2-bromo-1-(1-isopropoxyethoxy)indane, 2-bromo-1-(1-butoxyethoxy)indane, 2-bromo-1-(1-isobutoxyethoxy)indane, 2-bromo-1-(1-pentoxyethoxy)indane, 2-bromo-1-(1-isopentoxyethoxy)indane, 2-iodo-1-(1-methoxyethoxy)indane, 2-iodo-1-(1-ethoxyethoxy)indane, 2-iodo-1-(1-propoxyethoxy)indane, 2-iodo-1-(1-isopropoxyethoxy)indane, 2-iodo-1-(1-butoxyethoxy)indane, 2-iodo-1-(1-isobutoxyethoxy)indane, 2-iodo-1-(1-pentoxyethoxy)indane, 2-iodo-1-(1-isopentoxyethoxy)indane, 2-chloro-1-(2-tetrahydrofuranyloxy)indane, 2-bromo-1-(2-tetrahydrofuranyloxy)indane, 2-iodo-1-(2-tetrahydrofuranyloxy)indane or other novel compounds. Other examples include 2-chloro-1-(2-tetrahydropyranyloxy)indane, 2-bromo-1-(2-tetrahydropyranyloxy)indane, 2-iodo-1-(2-tetrahydropyranyloxy)indane or other novel compounds, 2-methane sulfonyloxy-1-methoxy indane and the like.

Typically, the indanyl ether represented by generic formula (I) is dissolved or suspended in an appropriate solvent and mixed under basic conditions to obtain the indenyl ether derivative represented by generic formula (II).

In order to obtain these basic conditions, lithium methoxide, lithium ethoxide, lithium tert-butoxide, sodium methoxide, sodium ethoxide, sodium tert-butoxide, sodium tert-pentoxide, potassium methoxide, potassium ethoxide, potassium tert-butoxide or other alkali metal alkoxides can be used.

Moreover, lithium hydroxide, lithium carbonate, sodium hydroxide, sodium carbonate, sodium bicarbonate, potassium carbonate, potassium hydroxide, potassium bicarbonate, or other hydroxides or carbonates of alkali metals can also be used.

The amounts of these basic compounds used is preferably equal to the moles of the indanyl ether represented by generic formula (I) or greater, and they may be used in excess, but the amount of alkali metal alkoxide in comparison to 1 mole of substrate should be 0.9 mole to 10 moles, preferably 1.0 mole to 3 moles, and more preferably 1.1 moles to 1.5 moles, while the amount of hydroxides or carbonates of alkali metals in comparison to 1 mole of substrate should be 0.9 mole to 20 moles, preferably 1.5 mole to 10 moles, and more preferably 2 moles to 4 moles.

Examples of the solvent that can be used include: water, alcohols or other polar protic solvents, dimethyl formamide, dimethyl sulfoxide, hexamethylene sulfonamide or other polar aprotic solvents, hexane, heptane, octane, decane or other aliphatic hydrocarbons, benzene, toluene, xylene, mesitylene or other aromatic hydrocarbons, dichloromethane, dichloroethane, chloroform, carbon tetrachloride, trichloroethylene, tetrachloroethylene or other aliphatic halogenated hydrocarbons, monochlorobenzene, dichlorobenzene or other aromatic halogenated hydrocarbons or other solvents that are inactive in the reaction. In addition, these solvents can also be used in combination. For example, the reaction proceeds homogeneously when miscible solvents are used, but heterogeneously when immiscible solvents are used.

This reaction is possible in the range from $-10°$ C. to $200°$ C., but it is preferably carried out in the temperature range from $10°$ C. to $150°$ C. and more preferably from $50°$ C. to $120°$ C. If the temperature is lower than this, the reaction proceeds slowly, and if the reaction temperature is too high, the yield decreases due to side reactions. However, if the reaction solvent is water or a heterogeneous system of water and a solvent that is immiscible with water (for example, a water-monochlorobenzene system), even though a hydroxide or carbonate of an alkali metal is used, they have low solubility in the organic layer, so the reaction does not proceed smoothly. In this case, by adding catalytic amounts of a quaternary ammonium halide or quaternary phosphonium halide, the reaction rate can be increased. These quaternary ammonium halides or quaternary phosphonium halides are known as phase-transfer catalysts. In addition to these compounds, other known phase-transfer catalysts include crown ethers and cryptands, and these ring compounds can also be used effectively in the reaction of the invention.

After the end of the reaction, the reaction liquid is cooled to room temperature, and, if the reaction liquid is immiscible with water, the reaction product of the indenyl ether derivative represented by generic formula (II) may be extracted by normal methods after rinsing with water and concentrating the solvent. In addition, if the reaction liquid is miscible with water, water may be added to the reaction liquid and extraction may be performed by normal methods such as catalytic extraction. Note that it is also possible to perform hydrolysis next without extracting the indenyl ether derivative represented by generic formula (II).

The indenyl ether derivative represented by generic formula (II) is subjected to hydrolysis under basic conditions or acidic conditions to obtain the 1-indanone desired. However, if hydrolysis is performed under basic conditions, the reaction progress is slow and the side reactions proceed simultaneously and the yield drops, so it is preferable to perform hydrolysis under acidic conditions. In order to achieve these acidic conditions, it is preferable to use sulfuric acid, hydrochloric acid, phosphoric acid, acetic acid or trifluroacetic acid, but the desired conditions can also be achieved by using perchloric acid, boron trifluoride, methanesulfonic acid, p-toluenesulfonic acid, zeolite, ion-exchange resins or other appropriate acidic substances. The amount used is preferably equal to or greater than the number of moles of catalyst or the indenyl ether derivative represented by generic formula (II). If the amount of acid used is too little, the reaction may not be completed.

In the case that sulfuric acid is used in order to achieve the acidic conditions, the reaction is possible at a sulfuric acid concentration of 0.001 mol % or greater, but it is preferable to perform the reaction at a sulfuric acid concentration from 0.005 mol % to 50 mol %, and more preferably from 0.01 mol % to 10 mol %. If the concentration is lower, the reaction progress is slow and the volume efficiency also becomes poor, and if higher, the yield decreases due to side reactions. Examples of the solvent that can be used include: water, alcohols or other polar protic solvents, dimethyl formamide, dimethyl sulfoxide, hexamethylene sulfonamide or other polar aprotic solvents, hexane, heptane, octane, decane or other aliphatic hydrocarbons, benzene, toluene, xylene, mesitylene or other aromatic hydrocarbons, monochlorobenzene, dichlorobenzene or other aromatic hydrocarbon halides, or other solvents that are inactive in the reaction. In addition, these solvents can also be used in combination. For example, the reaction proceeds homogeneously when miscible solvents are used, but heterogeneously when immiscible solvents are used.

The reaction is possible in the range from −20° C. to 150° C., but it is preferably carried out in the temperature range from 0° C. to 120° C. and more preferably from 10° C. to 50° C. If the temperature is lower than this, the reaction proceeds slowly, and if the reaction temperature is too high, the yield decreases due to side reactions.

After the end of the reaction, the reaction liquid is cooled to room temperature, and if the reaction liquid is immiscible with water, the reaction liquid may be rinsed with water and the reaction product of 1-indanone may be extracted as is by concentration and evaporation. In addition, if the reaction liquid is miscible with water, extraction may be performed by normal methods such as catalytic extraction.

The indanyl ether represented by generic formula (I) can be obtained by reacting the 2-haloindan-1-ol represented by generic formula (V) with the alkenyl ether represented by generic formula (VI) in the presence of an acid catalyst.

Examples of the 2-haloindan-1-ol represented by generic formula (V) include 2-chloroindan-1-ol, 2-bromoindan-1-ol, 2-iodoindan-1-ol and the like.

Examples of the alkenyl ether represented by generic formula (VI) include methyl vinyl ether, ethyl vinyl ether, n-propyl vinyl ether, isopropyl vinyl ether, n-butyl vinyl ether, isobutyl vinyl ether, n-amyl vinyl ether, isoamyl vinyl ether, 3,4-dihydro[2H]pyrane, 2,3-dihydrofuran and the like.

The amounts of these alkenyl ethers used compared to the 2-haloindan-1-ol represented by generic formula (V) is roughly 0.8 moles to 10 moles, but preferably 1.0 mole to 3.0 moles, and more preferably 1.0 moles to 1.2 moles.

In order to achieve these acidic conditions, it is preferable to use pyridinium p-toluenesulfonic acid, pyridinium trifluoromethanesulfonic acid, pyridinium 3-nitrobenzenesulfonic acid or other pyridinium salts, triethylamine hydrochloride, trimethylamine hydrochloride, triethylamine phosphate or other ammonium salts, sulfuric acid, hydrochloric acid, phosphoric acid, acetic acid, trifluroacetic acid, methanesulfonic acid or p-toluenesulfonic acid, but the desired conditions can also be achieved by using perchloric acid, boron trifluoride, zeolite, ion-exchange resins or other appropriate acidic substances. The amount used is preferably equal to or greater than the number of moles of catalyst or the 2-haloindan-1-ol represented by generic formula (V). If the amount of acid used is too little, the reaction may not be completed.

In the case that pyridinium p-toluenesulfonic acid is used in order to achieve the acidic conditions, the reaction is possible at a concentration compared to 2-haloindan-1-ol represented by generic formula (V) of 0.001 mol % or greater, but it is preferable to perform the reaction at a concentration from 0.005 mol % to 50 mol %, and more preferably from 0.01 mol % to 2 mol %. If the concentration is lower, the reaction progress is slow and the yield decreases due to side reactions. Examples of the solvent include: hexane, heptane, octane, decane or other aliphatic hydrocarbons, benzene, toluene, xylene, mesitylene or other aromatic hydrocarbons, dichloromethane, dichloroethane, chloroform, carbon tetrachloride, trichloroethylene, tetrachloroethylene or other aliphatic hydrocarbon halides, monochlorobenzene, dichlorobenzene or other aromatic hydrocarbon halides, or other solvents that are inactive in the reaction. In addition, these solvents can also be used in combination. For example, when miscible solvents are used, the reaction proceeds as a homogeneous system, but when immiscible solvents are also used, the reaction occurs as a heterogeneous system.

The reaction is possible in the range from −30° C. to 150° C., but it is preferably carried out in the temperature range from −20° C. to 100° C. and more preferably from 0° C. to 50° C. If the temperature is lower than this, the reaction proceeds slowly, and if the reaction temperature is too high, the yield decreases due to side reactions.

After the end of the reaction, the reaction liquid is cooled to room temperature, and if the reaction liquid is immiscible with water, after rinsing with water the solvent is concentrated and then the reaction product of indanyl ether represented by generic formula (I) may be extracted by ordinary methods. In addition, if the reaction liquid is miscible with water, extraction may be performed by normal methods such as catalytic extraction. Note that the reaction can be performed by performing the reaction that forms the indenyl ether derivative represented by generic formula (II) next without extracting the indanyl ether represented by generic formula (I).

By means of the invention, the useful substance 1-indanone represented by formula (III) can be obtained from the indenyl ether derivative represented by generic formula (II) derived from 2-haloindan-1-ol represented by generic formula (V) which is easily obtained industrially, and thus 1-indanone can be synthesized inexpensively, so the invention is industrially very valuable.

Note that by means of the invention, the indenyl ether represented by generic formula (I) and the indenyl ether derivative represented by generic formula (II) derived from 2-haloindan-1-ol represented by generic formula (V) can be converted to the final product of 1-indanone represented by formula (III) without intermediate isolation, so it can be industrialized extremely easily and is thus a highly useful manufacturing method.

PREFERRED EMBODIMENTS OF THE INVENTION

Here follows a detailed description of the invention made by means of preferred embodiments.

The analysis of reaction intermediates and products in the following preferred embodiments was performed by means of high-performance liquid chromatography (HPLC) and gas chromatography (GC).

High-performance Liquid Chromatography (HPLC) Conditions
Columns: YMC pack $C_8$ A202 (4.6$\phi$×150 mm)
Mobile phase: See the gradient data below.
Flow rate: 1 ml/minute
Detection: 254 nm
Temperature: 40° C.

TABLE 1

Gradient data

| Hold time (min.) | 0–5 | 5–15 | 15–25 | 25–30 |
|---|---|---|---|---|
| 0.01/3N $H_3PO_4$ | 80 | 80–10 | 10 | 10–80 |
| Acetonitrile | 20 | 20–90 | 90 | 90–20 |

Gas Chromatography (GC) Conditions
Columns: Glass columns (3.2$\phi$×2.1 mm)
Filler: 5% Silicone OV17 60/80 mesh Uniport HP
Detector: FID
Range: $10^2$
Carrier gas: $N_2$
Inlet and detector temperature: 270° C.
Initial temperature hold time: 0 minutes
Ultimate temperature hold time: 15 minutes
Column temperature: 100° C.→260° C.
Rate of temperature increase: 10° C./minute

EXAMPLE 1

Synthesis of 1-indanone from a Starting Material of trans-2-bromo-1-(1-ethoxyethoxy)indane [I: R=CH(OR$_2$)R$_1$: R$_1$=CH$_3$, R$_2$=CH$_2$CH$_3$, X=Br]

A stirrer, thermometer and reflux condenser were mounted to a 500-ml four-necked flask which was filled with 107 g (0.5 mol) of trans-2-bromoindan-1-ol, 1 g of the strongly acidic ion-exchange resin Nafion (registered trademark) NR50 (made by Fluka Fine Chemical Co.) and 100 ml of dichloromethane and cooled in a water bath to 14° C. While the mixture was stirred, 54.1 g (0.75 mol) of ethyl vinyl ether was added dropwise over one hour. After stirring for an additional 1.5 hours at 25° C., the strongly acidic ion-exchange resin was filtered. The filtrate was vacuum-concentrated to obtain 153.0 g of a yellow syrup. 30.6 g of this yellow syrup was purified by silica gel column chromatography (using chloroform as the extraction medium) to obtain 22.3 g of a yellow syrup of trans-2-bromo-1-(1-ethoxyethoxy)indane (giving a yield of 77.9%). The purity of this compound according to HPLC was 94.1% (surface area percentage). Its physical properties are given below.

$^1$H-NMR (CDCl$_3$, ppm, TMS): δ=7.19–7.44 (4H, m, arom), 5.36, 5.24 (1H, d, CH), 5.14, 5.00 (1H, q, CH), 4.54, 4.42 (1H, m, CH), 3.56–3.85 (3H, m, CH$_2$), 3.22 (H, q, CH), 1.44, 1.40 (3H, d, CH$_3$), 1.24–1.32 (3H, d, CH$_3$)

IR (neat, cm$^{-1}$): 2978.4 (C—H), 1124.6 (C—O—C), 1084.1 (C—O—C), 1057.1 (C—O—C)

A stirrer, thermometer and reflux condenser were mounted to a 200-ml four-necked flask which was filled with 25.5 g (0.089 mol) of trans-2-bromo-1-(1-ethoxyethoxy)indane and 100 ml of methanol and cooled in an ice-salt bath to 0° C. While the mixture was stirred, 11.8 g (0.22 mol) of sodium methoxide was added. The mixture was removed from the ice-salt bath and stirred for 12 hours at 68° C. The reaction liquid was cooled to 25° C., 100 ml of water was added and extraction was performed three times with 100 ml of dichloromethane. The dichloromethane layer was dried with anhydrous sodium sulfate and vacuum-concentrated to obtain 17.2 g of a reddish-brown oil of 1-(1-ethoxyethoxy)indene (giving a yield of 94.7%). The purity of this compound according to HPLC was 95.3% (surface area percentage). Its physical properties are given below.

$^1$H-NMR (CDCl$_3$, ppm, TMS): δ=7.20–7.49 (4H, m, arom), 5.39 (1H, q, CH), 5.36 (1H, m, CH), 3.84, 3.55 (2H, m, CH$_2$), 3.31 (2H, m, CH$_2$), 1.55 (3H, d, CH$_3$), 1.23 (3H, t, CH$_3$)

IR (neat, cm$^{-1}$): 2980.3 (C—H), 2889.6 (C—H), 1601.1 (C=C), 1116.9 (C—O—C).

A stirrer, thermometer and reflux condenser were mounted to a 100-ml four-necked flask which was filled with 6.94 g (0.034 mol) of 1-(1-ethoxyethoxy)indene, 34 ml of water, 2.04 g (0.034 mol) of acetic acid and 20 ml of methanol, and stirred for 18 hours at 25° C. The reaction liquid was extracted three times with 100 ml of dichloromethane. The dichloromethane layer was rinsed with 20 ml of a 1% aqueous solution of sodium carbonate, dried with anhydrous sodium sulfate and vacuum-concentrated to obtain 3.7 g of a red oil of 1-indanone (giving a yield of 82.4%). The purity of this oil according to gas chromatography (GC) was 85.6% (surface area percentage). The IR spectrum of this oil matches the IR spectrum of commercial 1-indanone.

EXAMPLE 2

Synthesis of 1-indanone from a Starting Material of cis-2-bromo-1-(2-tetrahydropyranyloxy)indane [I: R=2-tetrahydropyranyl group, X=Br]

A stirrer, thermometer and reflux condenser were mounted to a 200-ml four-necked flask which was filled with 21.3 g (0.1 mol) of cis-2-bromoindan-1-ol, 0.2 g of the strongly acidic ion-exchange resin Nafion (registered trademark) NR50 (made by Fuluka Co.) and 50 ml of dichloromethane and cooled in a water bath to 8° C. While the mixture was stirred, 29.4 g (0.35 mol) of 3,4-2H-dihydropyrane was added dropwise over 10 minutes. After stirring for an additional 4 hours at 25° C., the strongly acidic ion-exchange resin was filtered. The filtrate was vacuum-concentrated to obtain 32.9 g of a red syrup. This red syrup was purified by silica gel column chromatography (using chloroform as the extraction medium) to obtain 23.2 g of a syrup of cis-2-bromo-1-(2-tetrahydropyranyloxy)indane (giving a yield of 78.3%). The purity of this compound according to HPLC was 97.0% (surface area percentage). Its physical properties are given below.

$^1$H-NMR (CDCl$_3$, ppm, TMS): δ=7.22–7.5 (4H, m, arom), 5.16 (1H, d, CH), 4.97 (1H, d, CH), 4.87, 4.75 (1H, d, CH), 3.88, 3.61 (2H, m, CH$_2$), 3.40 (2H, m, CH$_2$), 1.52–2.00 (6H, m, CH$_2$)

IR (neat, cm$^{-1}$): 2943.6 (C—H), 1128.5 (C—O—C), 1074.5 (C—O—C), 1037.8 (C—O—C)

A stirrer, thermometer and reflux condenser were mounted to a 200-ml four-necked flask which was filled with 18.6 g (0.062 mo) of cis-2-bromo-1-(2-tetrahydropyranyloxy)indane and 100 ml of methanol and cooled in an ice-salt bath to 3° C. While the mixture was stirred, 6.7 g (0.124 mol) of sodium methoxide was added. The mixture was removed from the ice-salt bath and stirred for 5 hours at 25° C. and 1 hour at 68° C. The reaction liquid was cooled to 25° C., 200 ml of water was added and extraction was performed three times with 100 ml of dichloromethane. The dichloromethane layer was dried with anhydrous sodium sulfate and vacuum-concentrated to obtain 12.9 g of a reddish-brown oil of 1-(2-tetrahydropyranyloxy)

indene (giving a yield of 96.2%). The purity of this compound according to HPLC was 92.7% (surface area percentage). Its physical properties are given below.

$^1$H-NMR (CDCl$_3$, ppm, TMS): δ=7.20–7.50 (4H, m, arom), 5.58, 5.46 (1H, t, CH), 3.94, 3.62 (2H, m, CH$_2$), 3.39 (1H, dd, CH$_2$), 3.26 (1H, dd, CH$_2$), 1.52–2.13 (6H, m, CH$_2$)

IR (neat, cm$^{-1}$): 2943.3 (C—H), 1614.6 (C=C), 1126.5 (C—O—C).

A stirrer, thermometer and reflux condenser were mounted to a 100-ml four-necked flask which was filled with 9.52 g (0.044 mol) of 1-(2-tetrahydropyranyloxy)indene, 41 ml of water, 4.6 g (0.044 mol) of 35% hydrochloric acid and 20 ml of methanol, and stirred for 1 hour at 25° C. The reaction liquid was extracted three times with 20 ml of dichloromethane and the dichloromethane layer was dried with anhydrous sodium sulfate and vacuum-concentrated to obtain 5.7 g of a red oil of 1-indanone (giving a yield of 97.4%). The purity of this oil according to gas chromatography (GC) was 96.9% (surface area percentage). The IR spectrum of this oil matches the IR spectrum of commercial 1-indanone.

EXAMPLE 3

Synthesis of 1-indanone from a Starting Material of trans-2-methane sulfonyloxy-1-methoxy indane [I: R=CH$_3$, X=OSO$_2$CH$_3$]

A stirrer, thermometer and reflux condenser were mounted to a 500-ml four-necked flask which was filled with 200 ml of methanol and while stirring, 15.2 g (0.3 mol) of sodium methoxide was added. This liquid was cooled to 13° C. and 26.4 g (0.2 mol) of indene oxide dissolved in 100 ml of methanol was added dropwise over 6 hours. After stirring for an additional 3 days at 15° C., 100 ml of water was added to the reddish-brown reaction liquid which was vacuum-concentrated down to 100 ml. An additional 100 ml of water was added and extraction was performed twice with 100 ml of methylene chloride. The methylene chloride extract was dried with anhydrous sodium sulfate and vacuum-concentrated to obtain 35.7 g of a red oil of trans-1-methoxyindan-2-ol (giving a rough yield of 108.9%). The purity of this compound according to HPLC was 96.1% (surface area percentage). The IR spectrum of this compound matches the IR spectrum of commercial trans-1-methoxyindan-2-ol.

A stirrer, thermometer and reflux condenser were mounted to a 500-ml four-necked flask which was filled with 300 ml of dichloroethane, 35.7 g (0.2 mol) of trans-1-methoxyindan-2-ol and 22.3 g (0.22 mol) of triethylamine. While the mixture was kept at 25° C. in a water bath, 25.2 g (0.22 mol) of methanesulfonyl chloride was added dropwise over 2 hours and 40 minutes. The mixture was stirred for an additional 1.5 hours at 25° C. and then stirred for 1 hour at 40° C. The reaction liquid was cooled to 25° C. and then the reaction liquid was rinsed successively with 100 ml of water, 100 ml of a 5% aqueous solution of sodium carbonate and 100 ml of water, dried with a saturated brine solution and anhydrous sodium sulfate and vacuum-concentrated to obtain 47.8 g of a reddish-brown oil. This oil was subjected to silica gel column chromatography (using chloroform as the extraction medium) and the extract was vacuum-concentrated to obtain 43.8 g of yellow-orange crystals of trans-1-methoxy-2-methane sulfonyloxy indane (giving a yield of 90.5%). The purity of this compound according to gas chromatography (GC) was 98.8% (surface area percentage). Its physical properties are given below.
Melting point: 52.6–56.1° C.

$^1$H-NMR (CDCl$_3$, ppm, TMS): δ=7.20–7.43 (4H, m, arom), 5.31 (1H, m, CH), 4.96 (1H, d, CH), 3.58 (3H, s, OCH$_3$), 3.52 (1H, dd, CH$_2$), 3.09 (3H, s, SCH$_3$)

IR (KBr, cm$^{-1}$): 1334.9 (S=O), 1172.8 (S—O—C), 1095.7 (C—O—C), 962.6 (S—O—C).

A stirrer, thermometer and reflux condenser were mounted to a 500-ml four-necked flask which was filled with 200 ml of methanol and 12.1 g (0.05 mol) of trans-1-methoxy-2-methane sulfonyloxy indane, and cooled in an ice-salt bath to 0° C. The cream-colored slurry was stirred while 27 g (0.5 mol) of sodium methoxide was added. The reaction liquid was heated to 70° C., stirred for 6 hours, cooled to 25° C., 200 ml of water was added, and extraction was performed twice with 200 ml of methylene chloride and the methylene chloride layer was dried with anhydrous sodium sulfate and vacuum-concentrated to obtain 7.17 g of a reddish-brown oil of 1-methoxyindene (yield of 98.2%). The purity of this compound according to gas chromatography (GC) was 90.9% (surface area percentage). Its physical properties are given below.

$^1$H-NMR (CDCl$_3$, ppm, TMS): δ=7.19–7.43 (4H, m, arom), 5.26 (1H, t, CH), 4.96 (1H, d, CH), 3.86 (3H, s, OCH$_3$), 3.30 (2H, d, CH$_2$)

IR (neat, cm$^{-1}$): 1618.4 (C=C), 1130.4 (C—O—C), 1087.9 (C—O—C)

A stirrer, thermometer and reflux condenser were mounted to a 300-ml four-necked flask which was filled with 200 ml of dichloroethane, 10 ml of water, to which was added 10 ml (0.01 ml) of 2N sulfuric acid and the mixture was stirred for 1.5 hours at 25° C. The reddish-orange dichloroethane layer was separated, rinsed with 100 ml of water and then dried with anhydrous sodium sulfate and vacuum-concentrated to obtain 1.29 g of a red oil of 1-indanone (yield of 97.7%). The purity of this oil according to gas chromatography (GC) was 97.3% (surface area percentage). The IR spectrum of this oil matches the IR spectrum of commercial 1-indanone.

EXAMPLE 4

Synthesis of 1-indanone from a Starting Material of trans-2-chloro-1-(1-ethoxyethoxy)indane [I: R=CH(OR$_2$)R$_1$: R$_1$=CH$_3$, R$_2$=CH$_2$CH$_3$, X=Cl]

A stirrer, thermometer and reflux condenser were mounted to a 100-ml three-necked flask which was filled with 10.0 g (0.059 mol) of trans-2-chloroindan-1-ol, 13 ml of monochlorobenzene and 4.72 g (0.066 mol) of ethyl vinyl ether. While the mixture was stirred, 5.6 g (0.03 mol) of p-toluenesulfonic acid was added and stirred for 3 hours at 25° C. to form trans-2-chloro-1-(1-ethoxyethoxy)indane in the reaction system. Moreover, to the reaction liquid was added 123.4 g (0.77 mol) of a 25% aqueous solution of NaOH and 1.44 g (0.0035 mol) of tetrabutylammonium bromide and the mixture was stirred for 30 hours at 103° C. to form 1-(1-ethoxyethoxy)indene in the reaction system. The reaction liquid was separated into a monochlorobenzene layer and a water layer. To the monochlorobenzene layer were added 20 ml of water and 0.65 g (0.0065 mol) of 98% sulfuric acid and the mixture was stirred for 1 hour at 78° C. After the reaction, the reaction liquid was separated into a monochlorobenzene layer and a water layer, and the monochlorobenzene layer was rinsed twice with 100 ml of water. The monochlorobenzene layer was dried with anhydrous sodium sulfate and then vacuum-concentrated to obtain 6.93 g of a black oil of 1-indanone (giving a yield of 88.4%). The purity of this oil according to gas chromatography (GC) was 63.9% (surface area percentage). The IR spectrum of this oil matches the IR spectrum of commercial 1-indanone.

What is claimed is:

1. A method of manufacturing 1-indanone comprising the steps of reacting an indanyl ether represented by generic formula (I)

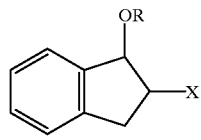
(I)

(where, in the formula, R is a straight-chain or branched-chain lower alkyl group with a carbon number of 1–5 or an alkoxyalkyl group represented by $CH(OR_2)R_1$; $R_1$ and $R_2$ are straight-chain or branched-chain lower alkyl groups with a carbon number of 1–5; $R_1$ and $R_2$ may be identical or different; $R_1$ and $R_2$ may also be connected to form a ring; X is a halogen atom or substituent sulfonyloxy group represented by $OSO_2R_3$; $R_3$ is a substituent or non-substituent phenyl group or a lower alkyl group with a carbon number of 1–5; OR and X may have the cis-arrangement or the trans- arrangement; and it may be in racemic form or optically active form) under basic conditions to give an indenyl ether derivative represented by generic formula (II)

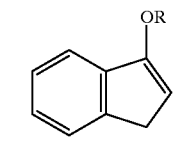
(II)

(where, in the formula, R is defined identically to that in generic formula (I) above) and hydrolyzing this to give the 1-indanone represented by generic formula (III)

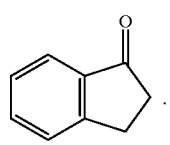
(III)

2. A method of manufacturing an indenyl ether derivative comprising the step of reacting an indanyl ether represented by generic formula (I)

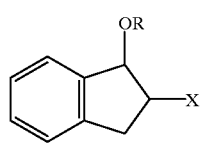
(I)

(where in the formula, R is a straight-chain or branched-chain lower alkyl group with a carbon number of 1–5 or an alkoxyalkye group represented by $CH(OR_2)R_1$; $R_1$ and $R_2$ are straight-chain or branched chain lower alkyl groups with a carbon number of 1–5; $R_1$ and $R_2$ may be identical or different; $R_1$ and $R_2$ may also be connected to form a ring; X is a halogen atom or substituent sulfonyloxy group represented by $OSO_2R_3$; $R_3$ is a substituent or non-substituent phenyl group or a lower alkyl group with a carbon number of 1–5; OR and X may have the cis-arrangement or the trans- arrangement; and it may be in racemic form or optically active form) under basic conditions to give an indenyl ether derivative represented by generic formula (II)

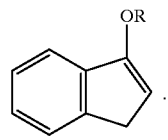
(II)

3. A method of manufacturing the indenyl ether derivative according to claim 1, wherein a compound represented by generic formula (IV)

MY (IV)

(where, in the formula, M is a positive quaternary ammonium ion or a positive quaternary phosphonium ion, and Y is a negative halide ion) is also present.

4. A method of manufacturing the indenyl ether derivative according to claim 1, wherein as the indanyl ether represented by the generic formula I, an indanyl ether is used in which R is an alkoxyalkyl group represented by $CH(OR_2)R_1$ where $R_1$ and $R_2$ are defined identically to those in generic formula (I) above) and X is a halogen atom.

5. A method of manufacturing the indenyl ether derivative according to claim 1, wherein an indenyl ether is used wherein, in generic formula (I), R is at least one alkoxyalkyl group selected from the group consisting of $CH(OCH_3)CH_3$, $CH(OC_2H_5)CH_3$, $CH(O(CH_2)_2CH_3)CH_3$, $CH(OCH(CH_3)_2)CH_3$, $CH(OCH_2CH(CH_3)_2)CH_3$, $CH(O(CH_2)_4CH_3)CH_3$, $CH(O(CH_2)_2CH(CH_3)_2)CH_3$, a 2-tetrahydropyranyl group and a 2-tetrahydrofuranyl group and X is a halogen atom.

6. A method of manufacturing the indenyl ether derivative according to claim 1, wherein at least one alkali metal alkoxide selected from the group consisting of lithium methoxide, lithium ethoxide, lithium tert-butoxide, sodium methoxide, sodium ethoxide, sodium tert-butoxide, sodium tert-pentoxide, potassium methoxide, potassium ethoxide, potassium tert-butoxide is used in order to obtain these basic conditions.

7. A method of manufacturing the indenyl ether derivative according to claim 1, wherein at least one hydroxide or carbonate of alkali metal selected from the group consisting of lithium hydroxide, lithium carbonate, sodium hydroxide, sodium carbonate, sodium bicarbonate, potassium carbonate, potassium hydroxide, potassium bicarbonate is used in order to obtain these basic conditions.

8. An indanyl ether derivative represented by generic formula (II)

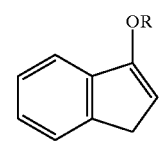
(II)

where, in the formula, R is $CH(OR_2)R_1$ (where $R_1$ and $R_2$ are straight-chain or branched-chain lower alkyl groups with a carbon number of 1–5; $R_1$ and $R_2$ may be identical or different; and $R_1$ and $R_2$ may also be connected to form a ring).

9. A method of manufacturing 1-indanone comprising the steps of manufacturing an indenyl ether derivative represented by generic formula (II)

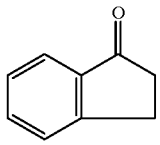

(where, in the formula, R is a straight-chain or branched-chain lower alkyl group with a carbon number of 1–5 or an alkoxyalkkyl group represented by $CH(OR_2)R_1$; $R_1$ and $R_2$ are straight-chained or branched-chain lower alkyl groups with a carbon number of 1–5; $R_1$ and $R_2$ may be identical or different; $R_1$ and $R_2$ may also be connected to form a ring) and hydrolyzing this under acidic conditions to give the 1-indanone represented by generic formula (III)

(III)

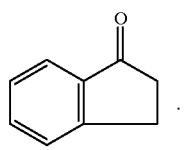

10. A method of manufacturing an indanyl ether comprising the step of reacting a 2-haloindan-1-ol represented by generic formula (V)

(V)

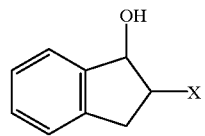

(where, in the formula, X is a halogen atom; OH and X may have the cis- arrangement or the trans- arrangement; and it may be in racemic form or optically active form) in the presence of an acidic catalyst with an alkenyl ether represented by generic formula (VI)

(VI)

$$R_1 - \underset{H}{C} = \underset{H}{C} - O - R_2$$

(where, in the formula, $R_1$ and $R_2$ are straight-chain or branched-chain lower alkyl groups with a carbon number of 1–5; $R_1$ and $R_2$ may be identical or different; and $R_1$ and $R_2$ may also be connected to form a ring) to give the 1-indanone represented by generic formula (I)

(I)

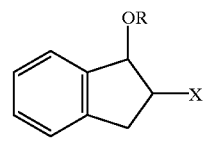

(where, in the formula, R is an alkoxyalkyl group represented by $CH(OR_2)R_1$; $R_1$ and $R_2$ are straight-chain or branched-chain lower alkyl groups with a carbon number of 1–5; $R_1$ and $R_2$ may be identical or different; $R_1$ and $R_2$ may also be connected to form a ring; X is a halogen atom; OR and X may have the cis- arrangement or the trans- arrangement; and it may be in racemic form or optically active form).

11. A method of manufacturing the indenyl ether derivative according to claim 10, wherein the alkenyl ether represented by generic formula (VI) is at least one selected from the group consisting of methyl vinyl ether, ethyl vinyl ether, n-propyl vinyl ether, isopropyl vinyl ether, n-butyl vinyl ether, isobutyl vinyl ether, n-amyl vinyl ether, isoamyl vinyl ether, 3,4-dihydropyrane and 2,3-dihydrofuran.

12. An indanyl ether represented by generic formula (I)

(I)

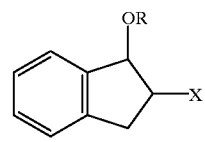

where, in the formula, R is $CH(OR_2)R_1$ (where $R_1$ is methyl and $R_2$ is ethyl and X is a halogen atom (OR and X may have the cis- arrangement or the trans- arrangement; and it may be in racemic form or optically active form).

* * * * *

UNITED STATES PATENT AND TRADEMARK OFFICE
CERTIFICATE OF CORRECTION

PATENT NO. : 6,127,579

DATED : October 3, 2000

INVENTOR(s) : Shigeru Nakano, Noriko Yoneta, Takashi Tate

It is certified that error appears in the above-identified patent and that said Letters Patent is hereby corrected as shown below:

In Claim 9, column 13, line 19, change "straight-chained" to --straight-chain--.

In Claim 11, column 14, line 34, change "3,4-dihydropyrane" to --3,4-dihydro[2H]pyrane--.

Signed and Sealed this

Seventeenth Day of April, 2001

NICHOLAS P. GODICI

*Attest:*

*Attesting Officer*  *Acting Director of the United States Patent and Trademark Office*